United States Patent [19]

Holtkamp, Sr.

[11] Patent Number: Plant 6,534

[45] Date of Patent: Jan. 17, 1989

[54] AFRICAN VIOLET PLANT NAMED CORINNA

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 56,414

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An African violet plant named Corinna, characterized by its star-shaped, very large light pink flowers with wavy edges; strong upright flower stems, producing a nice bouquet; profuse flowering; vigorous growth habit; medium green oval leaves; and non-dropping flowering habit.

1 Drawing Sheet

The present invention comprises a new and distinct cultivar of African violet plant, botanically known as *Saintpaulia ionantha,* and hereinafter referred to by the cultivar name Corinna.

The new cultivar was referred to during the breeding and selection process by the designation I16/6, and is a product of a planned breeding program. The new cultivar was originated from a cross made by applicant in a controlled breeding program in Haffen, Federal Republic of Germany. The female, or seed parent was a cultivar designated I16/6 red girl. The male, or pollen parent was a cultivar designated E148/1 and named Illinois, disclosed in U.S. Plant Pat. No. 4,870.

Corinna was discovered and selected by me as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Corinna has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Corinna which in combination distinguish this African violet as a new and distinct cultivar:

1. Very large light pink, star-shaped flowers with equally big petals, wavy edges.
2. Forms a nice bouquet on strong upright flower stems.
3. Each plant has 8–9 stems each of which carries 7 to 8 flowers.
4. Profuse flowering.
5. Seed capsule pushes slightly through.
6. Vigorous grower.
7. Plant saleable 10–11 weeks after potting.
8. Long-lasting, non-dropping flowers.

9. After maturity, the flowers dry off and remain on the peduncle without becoming infected by botrytis.
10. Medium green, oval leaves.
11. Up to 5 anthers composed of 10 anther cells.

The accompanying color photographic drawing shows a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken under natural light conditions at approximately 2:00 p.m. in Nashville, Tenn.

Botanical classification: *Saintpaulia ionantha,* Ramat., cv. Corinna.

Parentage:

*Male parent.*—E148/1, named Illinois.

*Female parent.*—I16/6.

Propagation: The new cultivar holds its distinguishing characteristics through successive propagations by leaf cuttings and by division of shoots.

Plant: From 9–11 cm tall when grown in pots, and approximately 25–29 cm in diameter when fully grown. The growth rate is vigorous.

Leaves.—Shape: Oval to spear-shaped. Diameter: 60–65 mm wide and 80–85 mm long. Texture: Velvety. Ribs and veins: Upperside visible, underside well pronounced, light green and shiny. Color (upper side): Yellow green 147A. Color (under side): Red purple veins; in between the veins the color is green 138D. Petioles: Green with purplish touch.

*Flowers.*—Buds: Pinkish green, bell-shaped, hairy, 7–9 mm before opening. Sepals: Five (5) in number, purple-green. Calyx: Funnel-shaped. Peduncle: Strong, upright, purplish brown.

*Individual flowers.*—Size: 50 to 55 mm in diameter. Shape: Star-shaped, 5 equally big petals with wavy edges. Color (upper side): Red 56A. Color (under side): Red 56B. Borne: Each of the 8–9 flower stems carries 7–9 and more flowers on strong, upright peduncles that are free standing above the leaves. Flowering habit: Flowers 10–11 weeks after potting.

*Reproductive organs.*—Stamens: Up to five (5) in number. Anthers: Up to five, composed of 10 anther cells, seed capsule pushes slightly through. Filaments: 3–4 long, yellowish green, with pink touch occasionally. Pollen color: Yellow 7A. Styles: 7–8 mm pink, base of ovary light green.

*Roots.*—Establish well, white, turning slightly brownish when older.

Disease resistance: Good.

General observations: Corinna is a very attractive, vigorous grower with very large, star-shaped, light pink flowers with wavy edges. All of the 5 single petals are of the same size and have a bright yellow center composed of up to 5 anthers. Approximately 10–11 weeks after potting the plant has developed 8–9 strong upright flower stems which carry 7–8 and more flowers. The flowers are on strong peduncles, free standing above the leaves. The flowers are long-lasting and non-dropping, and the seed capsule pushes slightly through.

I claim:

1. A new and distinct cultivar of African violet named Corinna, as described and illustrated, and particularly characterized by its star-shaped, very large light pink flowers with wavy edges; strong upright flower stems, producing a nice bouquet; profuse flowering; vigorous growth habit; medium green oval leaves; and long lasting and non-dropping flowering habit.

* * * * *

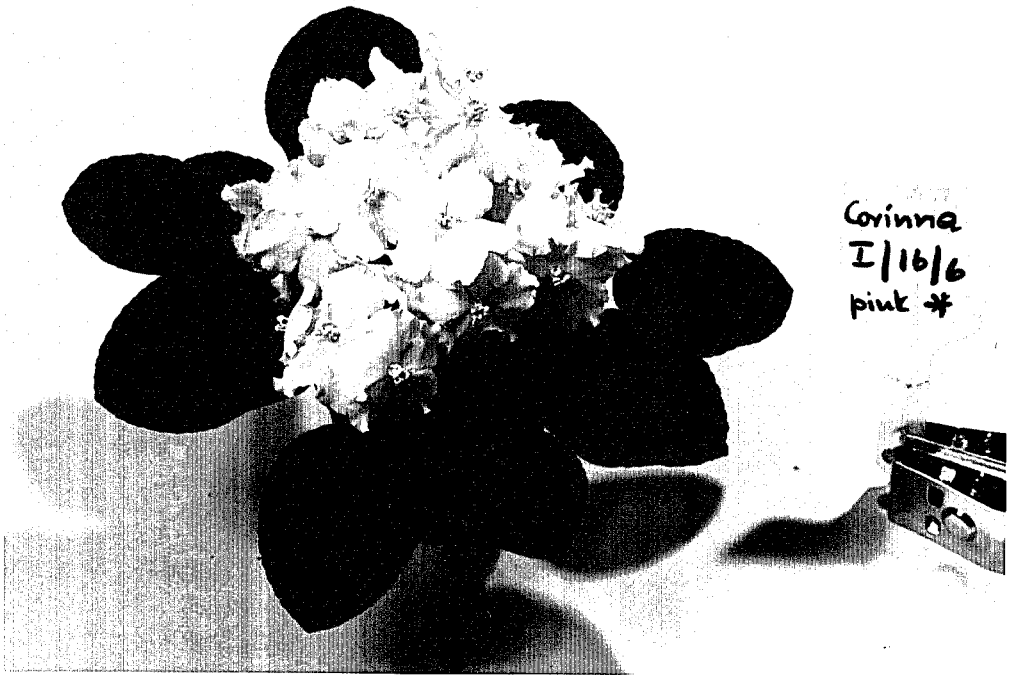
Corinna
I/16/6
pink #